(12) United States Patent
Yu

(10) Patent No.: US 11,315,440 B2
(45) Date of Patent: Apr. 26, 2022

(54) RESPIRATORY GATING PHANTOM DEVICE

(71) Applicant: National Chung Cheng University, Chia-Yi (TW)

(72) Inventor: Ying-Hao Yu, Chia-Yi (TW)

(73) Assignee: NATIONAL CHUNG CHENG UNIVERSITY, Min-Hsiung (TW)

(*) Notice: Subject to any disclaimer, the term of this patent is extended or adjusted under 35 U.S.C. 154(b) by 140 days.

(21) Appl. No.: 16/992,783

(22) Filed: Aug. 13, 2020

(65) Prior Publication Data

US 2022/0047239 A1   Feb. 17, 2022

(51) Int. Cl.
*G09B 23/28* (2006.01)
*A61B 6/03* (2006.01)
*A61N 5/10* (2006.01)
*A61B 6/00* (2006.01)

(52) U.S. Cl.
CPC ............ *G09B 23/286* (2013.01); *A61B 6/583* (2013.01); *A61N 5/1075* (2013.01); *G09B 23/288* (2013.01); *A61B 6/032* (2013.01); *A61B 6/541* (2013.01); *A61N 5/1068* (2013.01); *A61N 2005/1076* (2013.01)

(58) Field of Classification Search
CPC .............................. A61N 5/10; A61N 2005/10
See application file for complete search history.

(56) References Cited

U.S. PATENT DOCUMENTS

| | | | | |
|---|---|---|---|---|
| 7,842,929 | B2 * | 11/2010 | Krautim ............... | A61N 5/1048 378/65 |
| 8,110,811 | B2 * | 2/2012 | Krautim ............... | A61N 5/1048 378/207 |
| 8,227,762 | B2 * | 7/2012 | Krautim ............... | A61N 5/1048 378/207 |

(Continued)

FOREIGN PATENT DOCUMENTS

WO   WO-2018091265 A1 *  5/2018 ........... G09B 23/285

OTHER PUBLICATIONS

Liu, Yaxi et al. "Delivery of four-dimensional radiotherapy with TrackBeam for moving target using an AccuKnife dual-layer MLC: dynamic phantoms study." Journal of applied clinical medical physics vol. 10,2 21-33. Apr. 23, 2009, doi: 10.1120/jacmp.v10i2.2926 (Year: 2009).*

(Continued)

*Primary Examiner* — Thomas R Artman
(74) *Attorney, Agent, or Firm* — Muncy, Geissler, Olds & Lowe, P.C.

(57) ABSTRACT

A respiratory gating phantom device includes a first airbag, a second airbag, a first catheter, a second catheter, a fixture, and an air pressure gating device. The first catheter and the second catheter are respectively installed in the first airbag and the second airbag. The fixture is provided with a phantom tumor and adjustably installed in the first catheter or the second catheter, thereby installing the phantom tumor in the first catheter or the second catheter. The air pressure gating device, connected to the first airbag and the second (Continued)

airbag, inflates and deflates the first airbag and the second airbag to simulate breathing. The first catheter and the second catheter respectively move along three-dimensional direction and two-dimensional direction in response to motions of the first airbag and the second airbag.

11 Claims, 8 Drawing Sheets

(56) References Cited

U.S. PATENT DOCUMENTS

| | | | | |
|---|---|---|---|---|
| 8,535,061 | B2* | 9/2013 | Boutchko | G09B 23/28 434/262 |
| 9,218,752 | B2* | 12/2015 | Gillies | G09B 23/28 |
| 2009/0110140 | A1* | 4/2009 | Krautim | A61N 5/1048 378/18 |
| 2010/0167251 | A1* | 7/2010 | Boutchko | A61B 6/5247 434/267 |
| 2011/0067508 | A1* | 3/2011 | Krautim | A61N 5/1048 73/866.4 |
| 2012/0134471 | A1* | 5/2012 | Krautim | A61N 5/1048 378/65 |
| 2013/0108999 | A1* | 5/2013 | Gillies | G09B 23/30 434/272 |
| 2022/0047239 | A1* | 2/2022 | Yu | G09B 23/288 |

OTHER PUBLICATIONS

R. A. Isoardi, C. Comtat, V. Frouin, T. Delzescaux and R. Trebossen, "Simulating respiratory motion in whole-body PET imaging with the MCAT phantom," 2002 IEEE Nuclear Science Symposium Conference Record, 2002, pp. 1113-1115 vol. 2, doi: 10.1109/NSSMIC.2002.1239516. (Year: 2002).*

* cited by examiner

RESPIRATORY GATING PHANTOM DEVICE

BACKGROUND OF THE INVENTION

Field of the Invention

The present invention relates to a phantom device, particularly to a respiratory gating phantom device.

Description of the Related Art

Cancer is a group of diseases in which abnormal cells divide without control, often invading other tissues. According to the American Cancer Society, in 2007 in the United States alone there will have been an estimated 1,444,920 new cases of cancer. It is estimated that in that same period 559,650 people will die in the United States due to various forms of cancer. Many forms of treatment are available and continue to be discovered. One of these forms of treatment is radiation therapy which is used, often in combination with other types of treatment, on roughly half of all cancer sufferers.

Radiation is often utilized in the treatment of cancer in order to control malignant cells and shrink tumors. Due to its harmful effects, physicians often attempt to limit the radiation to other parts of the body. This is accomplished by focusing the radiation on the tumor itself. However, the radiation field often may include normal tissue around the tumor to allow for uncertainties in the position of the tumor. One cause of these uncertainties is the natural movement of organs in the body which cause the position and shape of the tumor to change. Unfortunately, by increasing the field of the radiation, the normal tissue can also be affected. Radiation to these areas may cause side effects during treatment, in a period of time after the treatment, or cumulative side effects from re-treatment. To avoid this result, shaped radiation beams are often aimed from several angles to intersect at the tumor. Because these beams do not change direction with the movement of the tumor, excess radiation is received in a marginal volume around and including the tumor and its possible spatial deformation and positions.

Newer techniques allow for radiation to be aimed such that it follows the movement of the tumor and synchronizes the delivery of the radiation with this movement to limit the excess radiation. The equipment for this process is very complex and even small deviations can have large repercussions. To avoid these deviations, the equipment must frequently be calibrated and the quality of the results must be assured.

In radiation protection, or health physics, a phantom is a device that simulates the human body or part of the human body and is used to calibrate or test the calibration of a detector that measures radiation emanating from within the body. Phantoms can be used in the calibration of radiation delivery devices. However, most phantoms do not provide an accurate representation of the movements internal to the human body and the movement of a tumor within the body. Presently, a phantom tumor is mechanically moved. For example, the phantom tumor is moved based on a sine waveform or a moving track recorded in advance. Thus, the moving track of the phantom tumor is different from that of the living tumor. In addition, the depth of the phantom tumor is not freely adjusted.

To overcome the abovementioned problems, the present invention provides a respiratory gating phantom device.

SUMMARY OF THE INVENTION

The present invention provides a respiratory gating phantom device, which uses two airbags as dual phantom lungs. The computed tomography images of the airbags are more similar to those of living lungs of a human body. The depth of a phantom tumor is freely adjusted in the airbag without affecting the inflating effect, thereby simulating the movement of the living tumor of a patient. The phantom lungs are controlled in a closed loop way in order to accurately simulate breathing of the patient.

In an embodiment of the present invention, a respiratory gating phantom device includes a first airbag, a second airbag, a first catheter, a second catheter, a fixture, and an air pressure gating device. The first airbag and the second airbag are surrounded by a thoracic model and used as phantom lungs. The thoracic model is connected with a spine model. The spine model has a cervical vertebrae portion. The first airbag and the second airbag are respectively penetrated with a first space and a second space. The first catheter is installed in the first space. The top of the first catheter is connected with the cervical vertebrae portion through at least two first connecting rods. The bottom of the first catheter is fixed to the first airbag. The second catheter is installed in the second space. The top of the second catheter is connected with the cervical vertebrae portion through one second connecting rod. The bottom of the second catheter is fixed to the second airbag. The fixture is provided with a phantom tumor and adjustably installed in the first catheter or the second catheter, thereby installing the phantom tumor in the first catheter or the second catheter. The air pressure gating device is connected to the first airbag and the second airbag and configured to inflate and deflate the first airbag and the second airbag to simulate breathing. The first catheter and the second catheter respectively move along three-dimensional direction and two-dimensional direction in response to motions of the first airbag and the second airbag.

In an embodiment of the present invention, the first catheter includes a first cylinder, a first cover, and a second cylinder. The two ends of the first cylinder respectively have a first opening and a second opening. The first cylinder is provided with first hooks therein. The first cover covers the first opening. The first cover is provided with the at least two first connecting rods. The two ends of the second cylinder respectively have a closed top surface and a third opening. The external side of the closed top surface is provided with second hooks thereon. The first cylinder sleeves the second cylinder through the second opening. The bottom of the second cylinder is fixed to the first airbag. The first hooks and the second hooks hook elastic elements. The fixture penetrates through the third opening. The fixture is adjustably installed in the second cylinder, thereby installing the phantom tumor in the second cylinder.

In an embodiment of the present invention, the first cover is penetrated with a gas hole. The air pressure gating device is connected to the gas hole, the air pressure gating device is configured to inflate the first cylinder and push the second cylinder. The elastic elements are configured to pull the second cylinder.

In an embodiment of the present invention, the second catheter includes a third cylinder and a second cover. The two ends of the third cylinder respectively have a fourth opening and a fifth opening. The bottom of the third cylinder is fixed to the second airbag. The second cover covers the fourth opening. The second cover is provided with the second connecting rod. The fixture penetrates through the fifth opening. The fixture is adjustably installed in the third cylinder, thereby installing the phantom tumor in the third cylinder.

In an embodiment of the present invention, the respiratory gating phantom device further includes a base, a light emitting diode, a digital camera, and a computer host. The base is arranged on the sternum model. The base has a first side and a second side, wherein the first side is opposite to the second side. The light emitting diode is arranged on the first side of the base. The digital camera, facing to the first side, is configured to capture and output the moving track of the light emitting diode. The computer host is coupled to the digital camera and the air pressure gating device and configured to receive the moving track. The computer host is configured to control the air pressure gating device based on the moving track and a given track.

Below, the embodiments are described in detail in cooperation with the drawings to make easily understood the technical contents, characteristics and accomplishments of the present invention.

DETAILED DESCRIPTION OF THE INVENTION

Figure 1A:
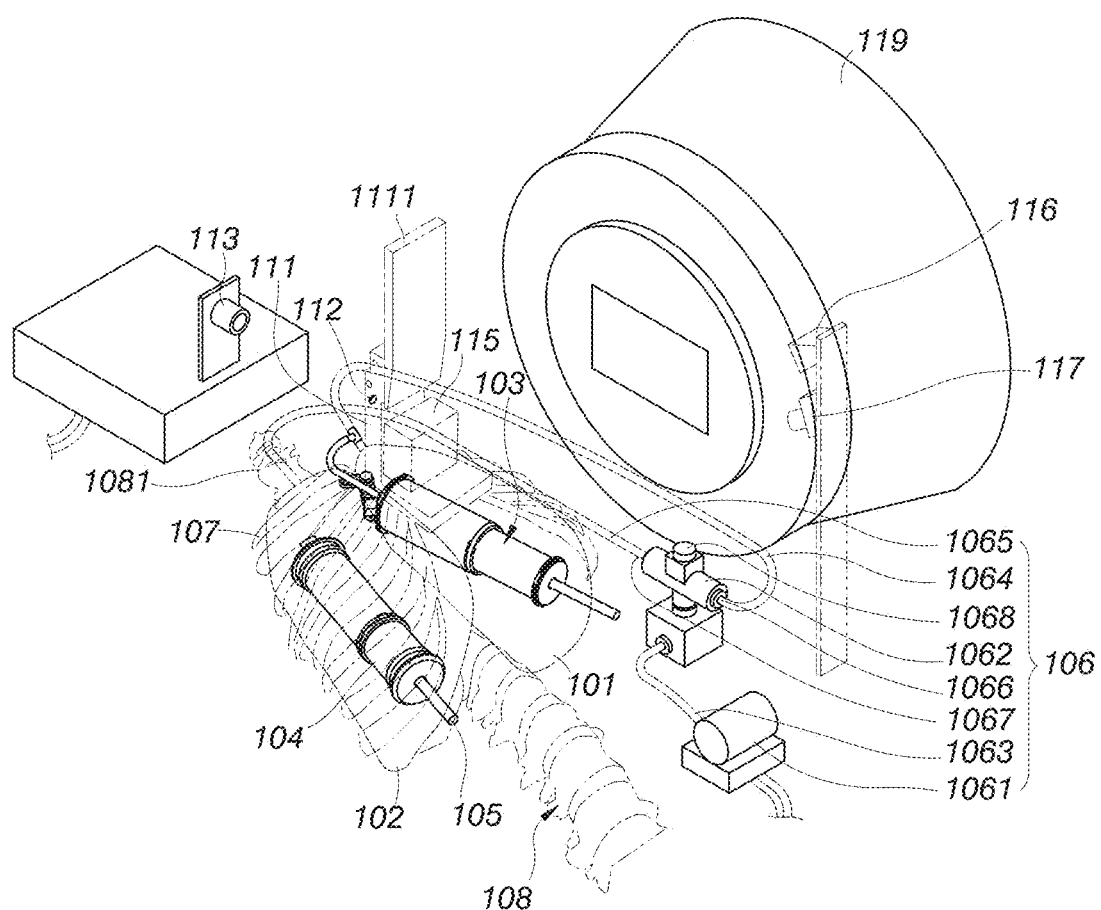
FIG. 1(a) is a diagram schematically illustrating a respiratory gating phantom device and a linear accelerator according to an embodiment of the present invention.

Reference will now be made in detail to embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, methods and apparatus in accordance with the present disclosure. It is to be understood that elements not specifically shown or described may take various forms well known to those skilled in the art. Many alternatives and modifications will be apparent to those skilled in the art, once informed by the present disclosure.

Unless otherwise specified, some conditional sentences or words, such as "can", "could", "might", or "may", usually attempt to express that the embodiment in the invention has, but it can also be interpreted as a feature, element, or step that may not be needed. In other embodiments, these features, elements, or steps may not be required.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment.

Certain terms are used throughout the description and the claims to refer to particular components. One skilled in the art appreciates that a component may be referred to as different names. This disclosure does not intend to distinguish between components that differ in name but not in function. In the description and in the claims, the term "comprise" is used in an open-ended fashion, and thus should be interpreted to mean "include, but not limited to." The phrases "be coupled to," "couples to," and "coupling to" are intended to compass any indirect or direct connection. Accordingly, if this disclosure mentioned that a first device is coupled with a second device, it means that the first device may be directly or indirectly connected to the second device through electrical connections, wireless communications, optical communications, or other signal connections with/without other intermediate devices or connection means.

In the following description, a respiratory gating phantom device will be provided. The respiratory gating phantom device uses two airbags as dual phantom lungs. The computed tomography images of the airbags are more similar to those of living lungs of a human body. The depth of a phantom tumor is freely adjusted in the airbag without affecting the inflating effect, thereby simulating the movement of the living tumor of a patient. The phantom lungs are controlled in a closed loop way in order to accurately simulate breathing of the patient.

Figure 1A:
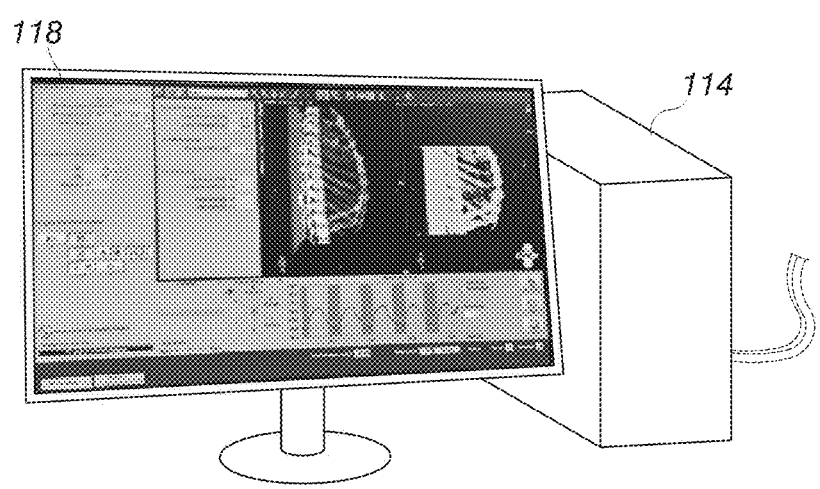
Figure 1B:
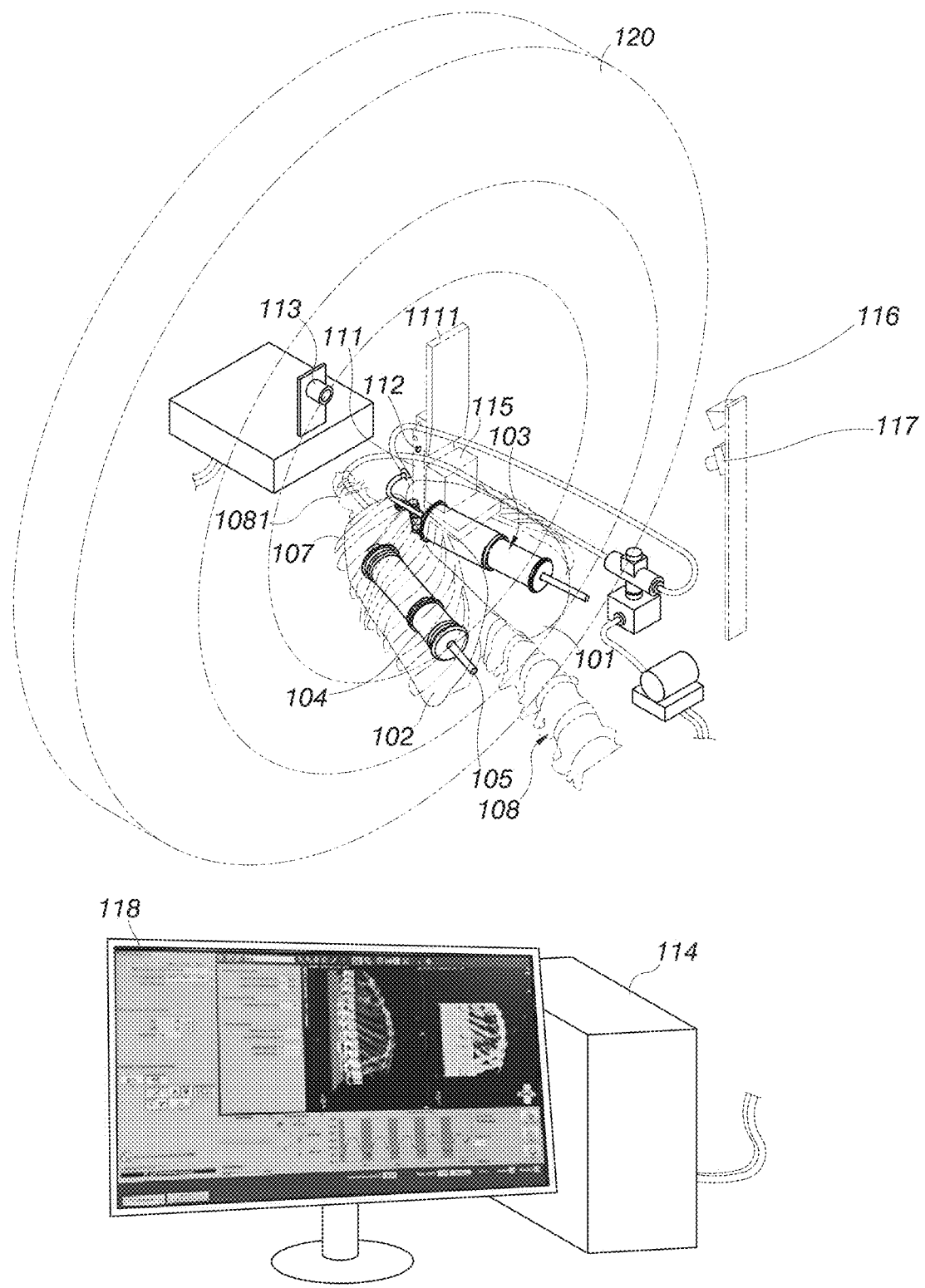
FIG. 1(b) is a diagram schematically illustrating a respiratory gating phantom device and a computer tomography (CT) device according to an embodiment of the present invention.
Figure 2:
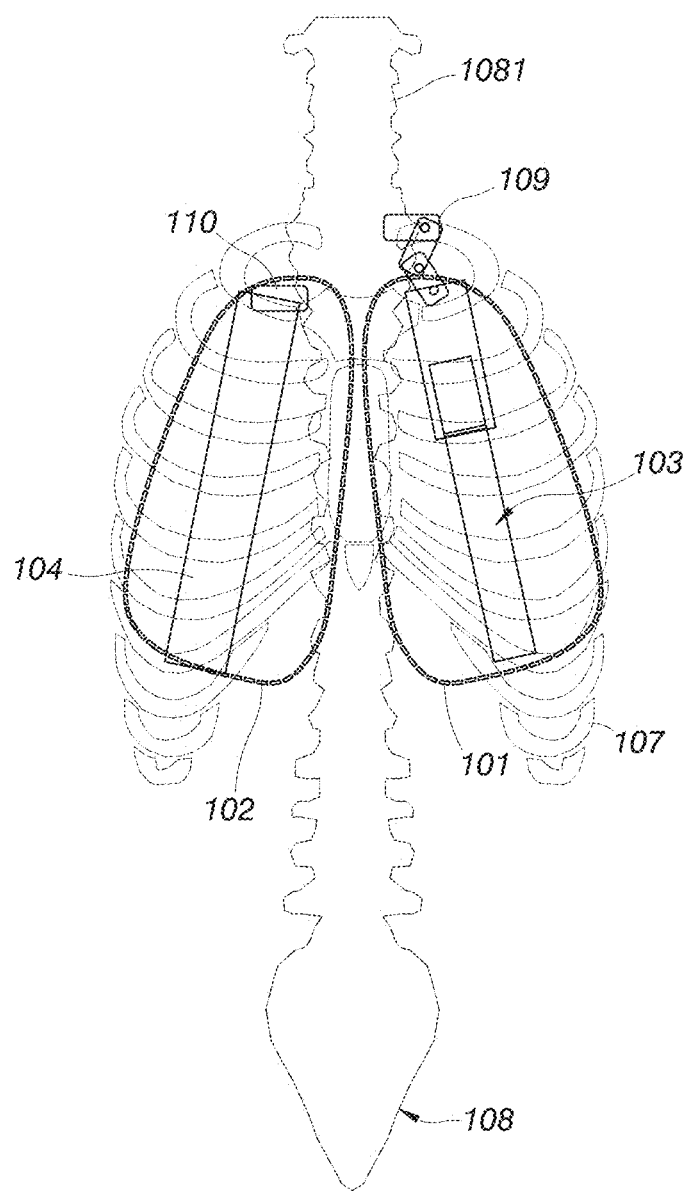
FIG. 2 is a diagram schematically illustrating a first airbag, a second airbag, a first catheter, a second catheter, first connecting rods, a second connecting rod, a thoracic model, and a spine model according to an embodiment of the present invention.

FIG. 1(a) is a diagram schematically illustrating a respiratory gating phantom device and a linear accelerator according to an embodiment of the present invention. FIG. 1(b) is a diagram schematically illustrating a respiratory gating phantom device and a computer tomography (CT) device according to an embodiment of the present invention. FIG. 2 is a diagram schematically illustrating a first airbag, a second airbag, a first catheter, a second catheter, first connecting rods, a second connecting rod, a thoracic model, and a spine model according to an embodiment of the present invention. Referring to FIG. 1(a), FIG. 1(b), and FIG. 2, the respiratory gating phantom device 10 includes a first airbag 101, a second airbag 102, a first catheter 103, a second catheter 104, a fixture 105, and an air pressure gating device 106. The first airbag 101 and the second airbag 102 are surrounded by a thoracic model 107 and used as phantom lungs. The thoracic model 107 is connected with a spine model 108. The spine model 108 has a cervical vertebrae portion 1081. The first airbag 101 and the second airbag 102 are respectively penetrated with a first space and a second space. The first catheter 103 is installed in the first space of the first airbag 101. The top of the first catheter 103 is connected with the cervical vertebrae portion 1081 through at least two first connecting rods 109. The bottom of the first catheter 103 is fixed to the first airbag 101. The second catheter 104 is installed in the second space of the second airbag 102. The top of the second catheter 104 is connected with the cervical vertebrae portion 1081 through one second connecting rod 110. The bottom of the second catheter 104 is fixed to the second airbag 102. The fixture 105 is provided with a phantom tumor and adjustably installed in the first catheter 103 or the second catheter 104, thereby installing the phantom tumor in the first catheter 103 or the second catheter 104. The installation of the fixture 105 and the phantom tumor will be described in cooperation with FIG. 3 and FIG. 5. The air pressure gating device 106 is connected to the first airbag 101 and the second airbag 102 and configured to inflate and deflate the first airbag 101 and the second airbag 102 to heave and simulate breathing. The thoracic model 107 moves along with the heave of the first airbag 101 and the second airbag 102. This way, the computed tomography images of the first airbag 101 and the second airbag 102 are more similar to those of living lungs of a human body. The first catheter 103 and the second catheter 104 respectively move along three-dimensional direction and two-dimensional direction in response to motions of the first airbag 101 and the second airbag 102. Specifically, the first catheter 103 can move vertically and horizontally. The second catheter 104 can move vertically.

In another embodiment of the present invention, the respiratory gating phantom device 10 may further include a base 111, a light emitting diode 112, a digital camera 113, and a computer host 114. The base 111, the light emitting diode 112, the digital camera 113, and the computer host 114 can cooperate with a reflective marker 115, an infrared emitter 116, and an optical camera 117 to operate. The optical camera 117 may be a charge-coupled device (CCD) camera, but the present invention is not limited thereto. The base 111 is arranged on the thoracic model 107. The base 111 has a first side and a second side, wherein the first side is opposite to the second side. The light emitting diode 112 is arranged on the base 111. The digital camera 113 faces to the light emitting diode 112 and the first side of the base 111. The base 111 and the light emitting diode 112 move along with the heave of the first airbag 101 and the second airbag 102. The user can use the base 111 and the light emitting diode 112 to observe the heave of the thoracic model 107. The digital camera 113 captures and outputs the moving track of the light emitting diode 112. The computer host 114 is coupled to the digital camera 113 and the air pressure gating device 106. The computer host 114 receives the moving track of the light emitting diode 112. In a closed loop way, The computer host 114 controls the air pressure gating device 106 to adjust the inflation and deflation of the first airbag 101 and the second airbag 102 based on the moving track of the light emitting diode 112 and a given track, thereby accurately simulating breathing of the patient. The given track may be set by an external device or built in the computer host 114 in advance. For example, the base 111 and the light emitting diode 112 can be alternatively placed on the chest of a patient. The digital camera 113 captures and records the moving track of the light emitting diode 112 on the base 111. Thus, the moving track of the light emitting diode 112 on the chest of the patient is used as the given track. The computer host 114 is coupled to a display 118. The display 118 may display the recorded given track or the moving track of the light emitting diode.

The reflective marker 115 is arranged on the second side of the base 111. The base 111 has a movable board 1111 that can move upward or downward and fasten the reflective marker 115 with any shape. The reflective marker 115 moves along with the heave of the first airbag 101 and the second airbag 102. The infrared emitter 116 emits infrared light to the reflective marker 115 to form light spots. The movable board 1111 prevents from reflecting the infrared light to the digital camera 113 to cause interference. The optical camera 117 faces to the reflective marker 115. The optical camera 117 is coupled to stereotactic body radiation therapy (SBRT) equipment. The SBRT equipment includes a linear accelerator 119 and a computer tomography (CT) device 120. The optical camera 117 captures the moving track of the light spot. The linear accelerator 119 or the CT device 120 emits an X-ray to the phantom tumor based on the moving track of the light spot.

In some embodiments of the present invention, the air pressure gating device 106 may include a gas pump 1061, a T-shaped tube 1062, an input gas tube 1063, a first gas tube 1064, and a second gas tube 1065. The gas pump 1061 is coupled to the computer host 114. The T-shaped tube 1062 is connected with the gas pump 1061 through the input gas tube 1063. The T-shaped tube 1062 has a first gas valve 1066, a second gas valve 1067, and a vent valve 1068. The first gas valve 1066 is connected with the first airbag 101 through the first gas tube 1064. The second gas valve 1067 is connected with the second airbag 102 through the second gas tube 1065. The computer host 114 controls the gas pump 1061 to inflate the first airbag 101 and the second airbag 102 through the T-shaped tube 1062, the input gas tube 1063, the first gas tube 1064, and the second gas tube 1065. The first airbag 101 and the second airbag 102 are deflated from the vent valve 1068.

Figure 3:
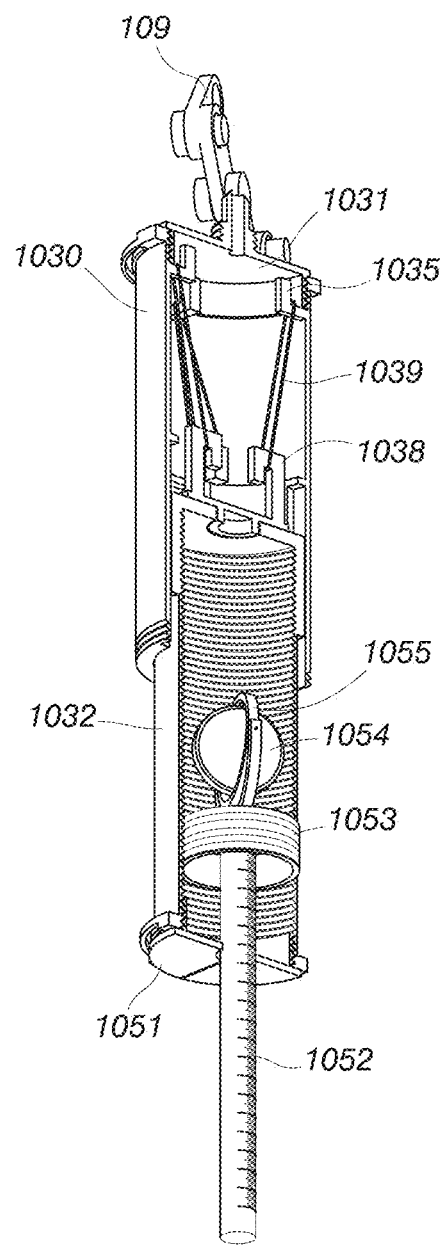
FIG. 3 is a diagram schematically illustrating the first catheter combined with a fixture and a phantom tumor according to an embodiment of the present invention.
Figure 4:
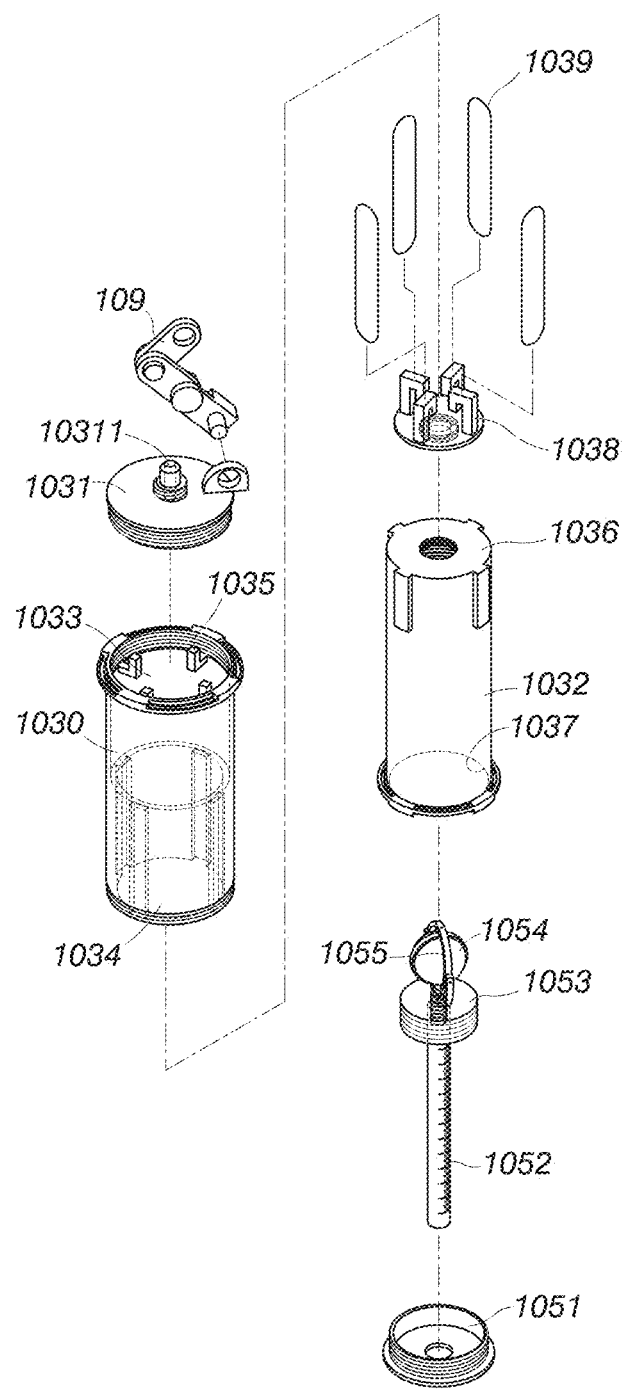
FIG. 4 is an exploded view of the first catheter combined with the fixture and the phantom tumor according to an embodiment of the present invention.

FIG. 3 is a diagram schematically illustrating the first catheter combined with a fixture and a phantom tumor according to an embodiment of the present invention. FIG. 4 is an exploded view of the first catheter combined with the fixture and the phantom tumor according to an embodiment of the present invention. Referring to FIG. 1, FIG. 3, and FIG. 4, the first catheter 103 is introduced as follows. The first catheter 103 may include a first cylinder 1030, a first cover 1031, and a second cylinder 1032. The two ends of the first cylinder 1030 respectively have a first opening 1033 and a second opening 1034. The first cylinder 1030 is provided with first hooks 1035 therein. The first cover 1031 covers the first opening 1033. The first cover 1031 is provided with the first connecting rods 109. The two ends of the second cylinder 1032 respectively have a closed top surface 1036 and a third opening 1037. The external side of the closed top surface 1036 is provided with second hooks 1038 thereon. The first cylinder 1030 sleeves the second cylinder 1032 through the second opening 1034. The bottom of the second cylinder 1032 is fixed to the first airbag 101. The first hooks 1035 and the second hooks 1038 hook elastic elements 1039, such as rubber bands or springs. The fixture 105 may penetrate through the third opening 1037. The fixture 105 is adjustably installed in the second cylinder 1032, thereby installing the phantom tumor in the second cylinder 1032.

The first cover 1031 may be penetrated with a gas hole 10311. The first gas tube 1064 of the air pressure gating device 106 is connected to the gas hole 10311. The gas pump 1061 of the air pressure gating device 106 inflates the first cylinder 1030 and pushes the second cylinder 1032. The elastic elements 1039 can pull the second cylinder 1032. Accordingly, the second cylinder 1032 elongates or retracts with respect to the first cylinder 1030 and moves the phantom tumor in response to the motions of the first airbag 101 and the second airbag 102.

In some embodiments of the present invention, the fixture 105 may include a fixed cover 1051, a ruler 1052, and a fixing element 1053. The fixed cover 1051 is fixed to the third opening 1037 of the first catheter 103. An end of the ruler 1052 is provided with the phantom tumor 1054 and another end of the ruler 1052 penetrates through the fixed cover 1051. The fixing element 1053 is annularly fixed to the ruler 1052 and adjustably installed on the inner sidewall of the second cylinder 1032. For example, the inner sidewall of the second cylinder 1032 is provided with a first thread and the outer sidewall of the fixing element 1053 is provided with a second thread. The fixing element 1053 is adjustably installed on the inner sidewall of the second cylinder 1032 through the first thread and the second thread. As a result, the depth of the phantom tumor 1054 is freely adjusted in the first airbag 101 without affecting the inflating effect, thereby simulating the movement of the living tumor of a patient. In addition, the outer bottom of the fixed cover 1051 has an indicating line for pointing to the scale of the ruler 1052. According to the indicating line and the scale of the ruler 1052, a user can know the depth of the phantom tumor 1054. The fixture 105 may further include a gimbal 1055 for supporting the phantom tumor 1054. The gimbal 1055 is installed on the ruler 1052.

Figure 5:
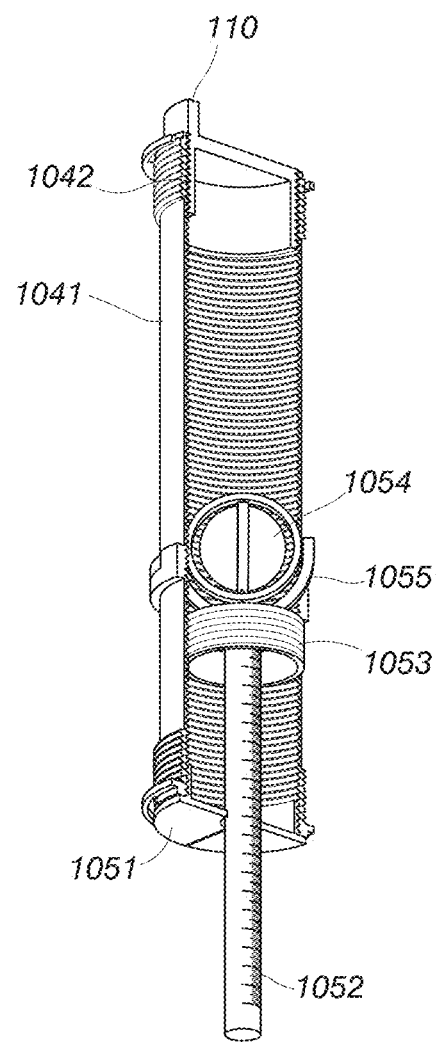
FIG. 5 is a diagram schematically illustrating the second catheter combined with a fixture and a phantom tumor according to an embodiment of the present invention.
Figure 6:
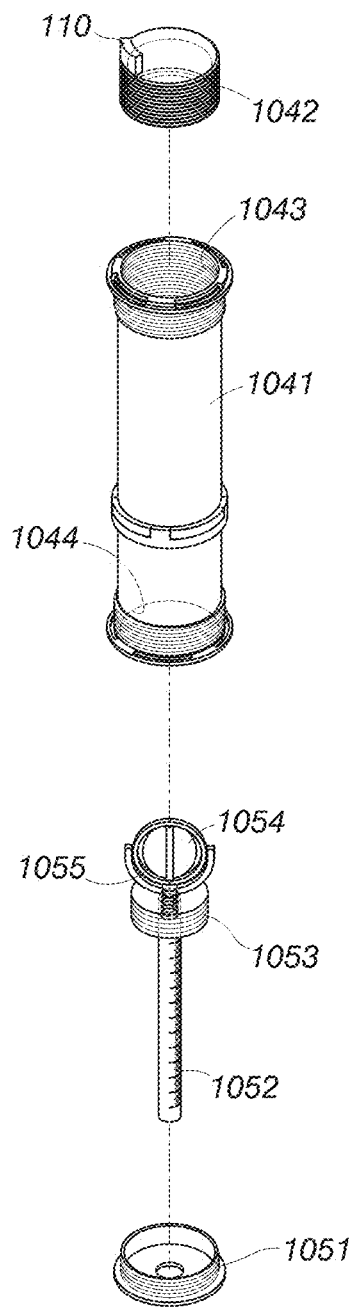
FIG. 6 is an exploded view of the second catheter combined with the fixture and the phantom tumor according to an embodiment of the present invention.

FIG. 5 is a diagram schematically illustrating the second catheter combined with a fixture and a phantom tumor according to an embodiment of the present invention. FIG. 6 is an exploded view of the second catheter combined with the fixture and the phantom tumor according to an embodiment of the present invention. Referring to FIG. 1, FIG. 5, and FIG. 6, the second catheter 104 is introduced as follows. The second catheter 104 may include a third cylinder 1041 and a second cover 1042. The two ends of the third cylinder 1041 respectively have a fourth opening 1043 and a fifth opening 1044. The bottom of the third cylinder 1041 is fixed to the second airbag 102. The second cover 1042 covers the fourth opening 1043. The second cover 1042 is provided with the second connecting rod 110. The fixture 105 penetrates through the fifth opening 1044. The fixture 105 may be adjustably installed in the third cylinder 1041, thereby installing the phantom tumor 1054 in the third cylinder 1041.

The fixed cover 1051 of the fixture 105 is fixed to the fifth opening 1044 of the second catheter 104. An end of the ruler 1052 is provided with the phantom tumor 1054 and another end of the ruler 1052 penetrates through the fixed cover 1051. The fixing element 1053 is annularly fixed to the ruler 1052 and adjustably installed on the inner sidewall of the third cylinder 1041. For example, the inner sidewall of the third cylinder 1041 is provided with a third thread. The fixing element 1053 is adjustably installed on the inner sidewall of the third cylinder 1041 through the third thread and the second thread. As a result, the depth of the phantom tumor 1054 is freely adjusted in the second airbag 102 without affecting the inflating effect, thereby simulating the movement of the living tumor of a patient.

Figure 7:
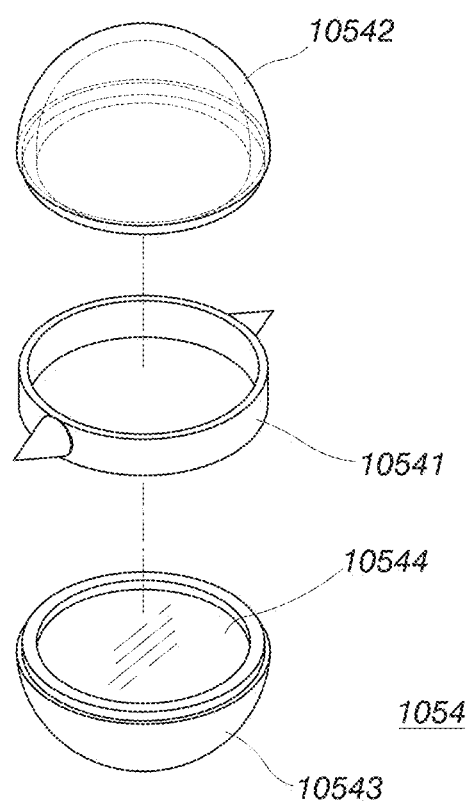
FIG. 7 is an exploded view of a phantom tumor according to an embodiment of the present invention.

FIG. 7 is an exploded view of a phantom tumor according to an embodiment of the present invention. Referring to FIG. 1 and FIG. 7, the phantom tumor 1054 is introduced as follows. The phantom tumor 1054 may include a holding ring 10541, a hollow semicircular sphere 10542, and a solid semicircular sphere 10543. An X-ray film 10544 is arranged on the solid semicircular sphere 10543. The hollow semicircular sphere 10542 and the solid semicircular sphere 10543 are respectively fixed to two opposite sides of the holding ring 10541. The hollow semicircular sphere 10542 or the solid semicircular sphere 10543 is fixed to the ruler or the gimbal of the fixture 105. The gimbal can balance the X-ray film 10544 when inflating or deflating the first airbag 101 and the second airbag 102. The X-ray film 10544 is used to determine whether the SBRT equipment emits an X-ray to the phantom tumor 1054.

According to the embodiments provided above, the respiratory gating phantom device uses two airbags as dual phantom lungs. The computed tomography images of the airbags are more similar to those of living lungs of a human body. The depth of a phantom tumor is freely adjusted in the airbag without affecting the inflating effect, thereby simulating the movement of the living tumor of a patient. The phantom lungs are controlled in a closed loop way in order to accurately simulate breathing of the patient.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A respiratory gating phantom device comprising:
a first airbag and a second airbag surrounded by a thoracic model and used as phantom lungs, wherein the thoracic model is connected with a spine model, the spine model has a cervical vertebrae portion, and the first airbag and the second airbag are respectively penetrated with a first space and a second space;
a first catheter installed in the first space, wherein a top of the first catheter is connected with the cervical vertebrae portion through at least two first connecting rods, and a bottom of the first catheter is fixed to the first airbag;
a second catheter installed in the second space, wherein a top of the second catheter is connected with the cervical vertebrae portion through one second connecting rod, and a bottom of the second catheter is fixed to the second airbag;
a fixture provided with a phantom tumor and adjustably installed in the first catheter or the second catheter, thereby installing the phantom tumor in the first catheter or the second catheter; and
an air pressure gating device connected to the first airbag and the second airbag and configured to inflate and deflate the first airbag and the second airbag to simulate breathing, wherein the first catheter and the second catheter respectively move along three-dimensional direction and two-dimensional direction in response to motions of the first airbag and the second airbag.

2. The respiratory gating phantom device of claim 1, wherein the first catheter comprises:
a first cylinder with two ends thereof respectively having a first opening and a second opening, wherein the first cylinder is provided with first hooks therein;
a first cover covering the first opening, wherein the first cover is provided with the at least two first connecting rods; and
a second cylinder with two ends thereof respectively having a closed top surface and a third opening, wherein an external side of the closed top surface is provided with second hooks thereon, the first cylinder sleeves the second cylinder through the second opening, a bottom of the second cylinder is fixed to the first airbag, the first hooks and the second hooks hook elastic elements, the fixture penetrates through the third opening, and the fixture is adjustably installed in the second cylinder, thereby installing the phantom tumor in the second cylinder.

3. The respiratory gating phantom device of claim 2, wherein the first cover is penetrated with a gas hole, the air pressure gating device is connected to the gas hole, the air pressure gating device is configured to inflate the first cylinder and push the second cylinder, and the elastic elements are configured to pull the second cylinder.

4. The respiratory gating phantom device of claim 2, wherein the elastic elements are rubber bands or springs.

5. The respiratory gating phantom device of claim 2, wherein the second catheter comprises:
- a third cylinder with two ends thereof respectively having a fourth opening and a fifth opening, and a bottom of the third cylinder is fixed to the second airbag; and
- a second cover covering the fourth opening, wherein the second cover is provided with the second connecting rod, the fixture penetrates through the fifth opening, and the fixture is adjustably installed in the third cylinder, thereby installing the phantom tumor in the third cylinder.

6. The respiratory gating phantom device of claim 1, wherein the fixture comprises:
- a fixed cover fixed to the first catheter or the second catheter;
- a ruler with an end thereof provided with the phantom tumor, and another end of the ruler penetrates through the fixed cover; and
- a fixing element annularly fixed to the ruler and adjustably installed on an inner sidewall of the first catheter or the second catheter.

7. The respiratory gating phantom device of claim 6, wherein the fixture further comprises a gimbal for supporting the phantom tumor, and the gimbal is installed on the ruler.

8. The respiratory gating phantom device of claim 1, wherein the air pressure gating device comprises:
- a gas pump; and
- a T-shaped tube connected with the gas pump through an input gas tube, wherein the T-shaped tube has a first gas valve, a second gas valve, and a vent valve, the first gas valve is connected with the first airbag through a first gas tube, the second gas valve is connected with the second airbag through a second gas tube, the gas pump is configured to inflate the first airbag and the second airbag through the T-shaped tube, the input gas tube, the first gas tube, and the second gas tube, and the first airbag and the second airbag are deflated from the vent valve.

9. The respiratory gating phantom device of claim 1, wherein the phantom tumor comprises:
- a holding ring; and
- a hollow semicircular sphere and a solid semicircular sphere respectively fixed to two opposite sides of the holding ring, wherein the hollow semicircular sphere or the solid semicircular sphere is fixed to the fixture, and an X-ray film is arranged on the solid semicircular sphere.

10. The respiratory gating phantom device of claim 1, further comprising:
- a base arranged on the thoracic model, wherein the base has a first side and a second side, and the first side is opposite to the second side;
- a light emitting diode arranged on the first side of the base;
- a digital camera, facing to the first side, configured to capture and output a moving track of the light emitting diode;
- a computer host coupled to the digital camera and the air pressure gating device and configured to receive the moving track, wherein the computer host is configured to control the air pressure gating device based on the moving track and a given track.

11. The respiratory gating phantom device of claim 10, wherein the base has a movable board that moves upward or downward and prevents from reflecting light to the digital camera.

* * * * *